US009068943B2

(12) United States Patent
Ivashin et al.

(10) Patent No.: US 9,068,943 B2
(45) Date of Patent: Jun. 30, 2015

(54) CHEMICAL ANALYSIS USING HYPHENATED LOW AND HIGH FIELD ION MOBILITY

(75) Inventors: Dmitriy V. Ivashin, Peabody, MA (US); Saïd Boumsellek, San Diego, CA (US)

(73) Assignee: Implant Sciences Corporation, Wilmington, MA (US)

( * ) Notice: Subject to any disclaimer, the term of this patent is extended or adjusted under 35 U.S.C. 154(b) by 568 days.

(21) Appl. No.: 13/066,894

(22) Filed: Apr. 27, 2011

(65) Prior Publication Data
US 2012/0273669 A1    Nov. 1, 2012

(51) Int. Cl.
H01J 49/40    (2006.01)
G01N 27/62    (2006.01)
H01J 49/00    (2006.01)

(52) U.S. Cl.
CPC .......... *G01N 27/626* (2013.01); *H01J 49/0036* (2013.01)

(58) Field of Classification Search
CPC .............. G01N 27/624; G01N 27/622; G01N 30/7206; G01N 21/68; H01J 49/004; H01J 49/40; H01J 49/00; H01J 49/009; H01J 49/0031; H01J 49/025
USPC .......... 250/281, 282, 286, 287, 294, 298, 299
See application file for complete search history.

(56) References Cited

U.S. PATENT DOCUMENTS

| | | | |
|---|---|---|---|
| 5,420,424 A | 5/1995 | Carnahan et al. | |
| 5,801,379 A | 9/1998 | Kouznetsov | |
| 6,809,313 B1 | 10/2004 | Gresham et al. | |
| 7,119,328 B2 | 10/2006 | Kaufman et al. | |
| 7,223,967 B2 | 5/2007 | Guevremont et al. | |
| 7,368,709 B2 | 5/2008 | Guevremont | |
| 7,399,958 B2 | 7/2008 | Miller et al. | |
| 7,714,284 B2 | 5/2010 | Miller et al. | |
| 7,838,823 B1 | 11/2010 | Pfiefer et al. | |
| 2003/0038235 A1 | 2/2003 | Guevremont et al. | |
| 2003/0089847 A1 | 5/2003 | Guevremont et al. | |

(Continued)

FOREIGN PATENT DOCUMENTS

SU    1337934 A2    9/1987

OTHER PUBLICATIONS

Pollard, Matthew J., et al., "Ion mobility spectrometer—field asymmetric ion mobility spectrometer-mass spectrometry", International Journal for Ion Mobility Spectrometry, vol. 14, No. 1, Mar. 9, 2011, XP55028073, ISSN: 1435-6163.

(Continued)

*Primary Examiner* — Nicole Ippolito
*Assistant Examiner* — Hanway Chang
(74) *Attorney, Agent, or Firm* — Muirhead and Saturnelli, LLC

(57) ABSTRACT

Using combined orthogonal techniques, such as low (IMS) and high (FAIMS) field mobility techniques, offers several advantages to ion detection and analysis techniques including low cost, no vacuum required, and the generation of 2-D spectra for enhanced detection and identification. Two analytical devices may be operated in different modes, which results in overall flexibility by adapting the hyphenated instrument to the application's requirements. With the IMS-FAIMS hardware level flexibility, the instruments may be configured and optimized to exploit different trade-offs suitable for a variety of detection scenarios of for different lists of target compounds.

22 Claims, 12 Drawing Sheets

(56) References Cited

U.S. PATENT DOCUMENTS

| | | |
|---|---|---|
| 2005/0051719 A1 | 3/2005 | Miller et al. |
| 2005/0109930 A1 | 5/2005 | Hill et al. |
| 2007/0176092 A1 | 8/2007 | Miller et al. |
| 2008/0073502 A1 | 3/2008 | Schneider et al. |
| 2008/0142700 A1 | 6/2008 | Dahl et al. |
| 2008/0179515 A1 | 7/2008 | Sperline |
| 2008/0237458 A1 | 10/2008 | Wang |
| 2009/0278040 A1 | 11/2009 | Wu |
| 2010/0207022 A1 | 8/2010 | Tang et al. |
| 2011/0133076 A1 | 6/2011 | Miller et al. |
| 2011/0260053 A1 | 10/2011 | Atkinson et al. |

OTHER PUBLICATIONS

Tang, Keqi, et al., "Two-Dimensional Gas-Phase Separations Coupled to Mass Spectrometry for Analysis of Complex Mixtures", Analytical Chemistry, vol. 77, No. 19, Oct. 1, 2005, XP55007024, ISSN: 0003-2700.

A.D. Appelhans and D.A. Dahl, "SIMION ion optics simulation at atmospheric pressure," *Int. J. Mass. Spectrom*, 244 (2005), pp. 1-14.

U.S. Appl. No. 11/941,939, filed Nov. 17, 2007, Boumsellek et al.

I. A. Buryakov et al., "A new method of separation of multi-atomic ions by mobility at atmospheric pressure using a high-frequency amplitude-asymmetric strong electric field," International Journal of Mass Spectrometry and Ion Processes, vol. 128, Issue 3, Oct. 9, 1993, pp. 143-148.

M. J. Pollard et al., "Ion mobility spectrometer: field asymmetric ion mobility spectrometer-mass spectrometry," Int. J. Ion Mobil. Spec., Springer-Verlag, Mar. 9, 2011, 8 pp.

A. A. Shvartsburg et al., "Optimization of the Design and Operation of FAIMS Analyzers," J. Am. Soc. Mass. Spectrom. 2005, 16, Nov. 23, 2004, pp. 2-12.

E. V. Krylov, "Pulses of Special Shapes Formed on a Capacitive Load," Instruments and Experimental Techniques, vol. 40, No. 5, 1997, pp. 628-631.

E. V. Krylov, et al., "Selection and generation of waveforms for differential mobility spectrometry," Review of Scientific Instruments, 81, 024101 (2010), 11 pp.

R. Guevremont, "High-Field Asymmetric Waveform Ion Mobility Spectrometry (FAIMS)," Canadian Journal of Analytical Sciences and Spectroscopy, vol. 49, No. 3, 2004, pp. 105-113.

"Application Circuits of Switch Mode Power Transformers," Butler Winding, retrieved from <<http://www.butlerwinding.com>> on Nov. 8, 2010, 3 pp.

400

CH1 vertical position – 1.04 divs (-52.0V)

CHEMICAL ANALYSIS USING HYPHENATED LOW AND HIGH FIELD ION MOBILITY

TECHNICAL FIELD

This application is related to the field of chemical analysis and, in particular, ion mobility spectrometry.

BACKGROUND OF THE INVENTION

In field applications, chemical analysis instruments may be confronted with various complex mixtures regardless of indoor or outdoor environments. Such mixtures may cause instrument contamination and confusion due to the presence of molecular interferents producing signatures that are either identical to that of the chemical compounds of interest or unresolved by the analytical instrument due to its limited resolution. An interferent can also manifest its presence by affecting the limit of detection of the compound of interest. A multi-stage analysis approach may therefore be used to reduce the chemical noise and produce enough separation for deterministic detection and identification. The multi-stage analysis may include either a single separation technique such as mass spectrometry (MS) in $MS^n$ instruments or a combination of different separation techniques. These are called orthogonal techniques since, even though they may operate in tandem, they measure different properties of the same molecule by producing multi-dimensional spectra hence increasing the probability of detection and accuracy of detection. For field instruments, such techniques may be physically and operationally integrated in order to produce complementary information hence improving overall selectivity without sacrificing speed and sensitivity.

In the area of trace explosives detection, ion mobility spectrometry may be commonly used at passenger checkpoints in airports. The technique relies on the availability of sufficient explosives residue (particles and/or vapor) on the passenger skin, clothing, and personnel items to signal a threat. The assumption being that due to their high sticking coefficient it is difficult to avoid contamination by explosives particles during the process of handling a bomb. The same high sticking coefficient results in extremely low vapor pressures and hence makes their detection difficult. The acquisition of vapor and/or particle samples may be achieved by either swiping "suspect" surfaces of luggage or persons, or in the case of portals and/or by sending pulses of compressed air intended to liberate particles off the person's clothing, skin, shoes etc. . . . . In both cases the sample is introduced into an ion mobility spectrometer (IMS) for analysis.

Ion mobility spectrometry utilizes relatively low electric fields to propel ions through a drift gas chamber and separate these ions according to their drift velocity. In IMS, the ion drift velocity is proportional to the field strength at low electric fields (~200 V/cm), and thus an ion's mobility (K) is independent of the applied field. In the IMS both analyte and background molecules are typically ionized using radioactive alpha or beta emitters and the ions are injected into a drift tube with a constant low electric field (300 V/cm or less) where they are separated on the basis of their drift velocity and hence their mobility. The mobility is governed by the ion collisions with the drift gas molecules flowing in the opposite direction. The ion-molecule collision cross section depends on the size, the shape, the charge, and the mass of the ion relative to the mass of the drift gas molecule. The resulting chromatogram is compared to a library of known patterns to identify the substance collected. Since the collision cross section depends on more than one ion characteristic, peak identification is not unique. IMS systems measure a secondary and less specific property of the target molecule—the time it takes for the ionized molecule to drift through a tube filled with a viscous gas under an electric field—and the identity of the molecule is inferred from the intensity vs time spectrum. Since different molecules may have similar drift times, IMS inherently has limited chemical specificity and therefore is vulnerable to interfering molecules.

High-field asymmetric waveform ion mobility spectrometry (FAIMS) is an emerging detection technology which can operate at atmospheric pressure to separate gas-phase and detect ions, as first described in detail by Buryakov, I. A.; Krylov, E. V.; Nazarov, E. G.; Rasulev, U. K., International Journal of Mass Spectrometry and Ion Processes 1993, 128 (3), pp. 143-148, which is incorporated herein by reference. FAIMS separates ions by utilizing the mobility differences of ions at high and low fields. Compared to conventional ion mobility, FAIMS operates at much higher fields (~10,000 V/cm) where ion mobilities become dependent on the applied field and are better represented by $K_h$, a non-constant high-field mobility term. Variations in $K_h$ from the low-field K, and the compound-dependence of that variation aids FAIMS in its separation power. FAIMS utilizes a combination of alternating current (AC) and direct current (DC) voltages to transmit ions of interest and filter out other ions, thus improving specificity, and decreasing the chemical noise. FAIMS can reduce false positives, since two different compounds having the same low-field mobility can often be distinguished in a high-field environment.

Ions are separated in FAIMS by their difference in mobility at high ($K_h$) and at low (K) electric fields. At a constant gas number density, N, the non-linear dependence of an ion's mobility in high electric fields can be described by $$K_h(E)=K_0[1+\alpha(E/N)^2+\beta(E/N)^4+\ldots] \quad \text{Equation (1)}$$

where $K_0$ is the ion mobility coefficient at zero electric field and $\alpha$ and $\beta$ describe the dependence of the ion's mobility at a high electric field in a particular drift gas.[3] This equation is an infinite series, but at realistic field intensities the terms above the $4^{th}$ order become insignificant. FAIMS cells are commonly comprised of two parallel electrodes, one typically held at a ground potential while the other has an asymmetric waveform applied to it. A commonly used asymmetric waveform, described by V(t) in Equation 2, includes a high-voltage component (also referred to as $V_1$ or dispersion voltage [DV]) which lasts for a short period of time ($t_1$) relative to a longer lasting ($t_2$) low-voltage component ($V_2$) of opposite polarity. Most FAIMS work up to date has employed a sinusoidal wave, plus its first harmonic at twice the frequency, as shown in Equation 2, where ω is the frequency in radians per second.

$$V(t)=(0.61)V_1\sin(\omega t)+(0.39)V_1\sin(2\omega t-\pi/2)\ldots \quad \text{Equation (2)}$$

The waveform is constructed so that the voltage-time product applied to the electrode is equal to zero, as displayed in Equation 3.

$$V_1t_1+V_2t_2=0 \quad \text{Equation (3)}$$

At high electric fields, the application of this waveform will cause an ion to experience a net drift toward one of the electrodes. Ions passing between the electrodes encounter this displacement because the ion's mobility during the high-voltage component ($K_h$) is different than that from the low-voltage mobility (K). In other words, the ion will move a different distance during the high-voltage portion than during the low-voltage portion. This ion will continue to migrate towards one of the electrodes and subsequently be lost unless a DC compensation voltage (CV) is applied to offset the drift. The CV values required to offset the drift of different ions will be different if the $K_h/K$ ratio of the ions are different. Thus, a mixture of compounds can be successfully separated by scanning the CV, allowing each compound to transmit at its characteristic CV, creating a CV spectrum.

When higher electric fields are applied to the FAIMS electrodes, an ion can have three possible changes in ion mobility. The mobility of type A ions increases with increasing electric field strength, the mobility of type C ions decreases, and the mobility of type B ions increases initially before decreasing at yet higher fields. Most low-mass ions (<m/z 300) are type A ions, whereas most high-mass ions are type C ions.

In addition to stand-alone use, FAIMS devices may be used to filter ions prior to analyses with mass spectrometry (MS) devices and/or drift tube IMS devices, and reference is made, for example, to U.S. Patent App. Publication No. 2010/0207022 A1 to Tang et al, published Aug. 19, 2010, entitled "Platform for Field Asymmetric Waveform Ion Mobility Spectrometry with Ion Propulsion Modes Employing Gas Flow and Electric Field," which is incorporated herein by reference. Tang et al. principally discuss multiple device instruments stages using a FAIMS device coupled to a subsequent device, such as an IMS or MS device, and in which the FAIMS device may be rapidly switched on or off to enable more sensitive analyses using the other stage(s). Paragraph [0010] of Tang et al. suggests that in such multiple device instrument stages it is possible for the other stage(s) to precede the FAIMS device; however, this discussion in Tang et al. is still directed towards the goal of providing a method for effective, rapid and convenient switch-off of the FAIMS separation in hybrid platforms to enable more sensitive analyses using the other stage(s).

Accordingly, it would be desirable to provide a system that provides for flexible operation to handle a variety of detection scenarios and that provides for enhanced chemical detection and identification capabilities.

SUMMARY OF THE INVENTION

According to the system described herein, a chemical detection and analysis system includes an ion mobility spectrometer (IMS) device having a drift tube that includes a first end with a sample inlet and a second end that is downstream from the first end. Ions from ionization of a sample input via the sample inlet are introduced into the drift tube. A gate grid is coupled to the second end of the drift tube. A high field asymmetric waveform ion mobility spectrometer (FAIMS) device is coupled downstream from the gate grid, wherein the ions from the drift tube are selectively gated for analysis by the FAIMS device via control of at least one voltage pulse to the gate grid. The FAIMS device may be coupled orthogonally to a flow direction of the ions through the drift tube of the IMS device. Control of the at least one voltage pulse to the gate grid may correspond to drift time of an ion of interest. The FAIMS device may include a circuit that drives the FAIMS device using an asymmetrical waveform, such as a rectangular waveform, although other asymmetrical waveforms may also be used. The system may operate in at least two operational modes corresponding to operations of the IMS device and the FAIMS device. The FAIMS device may have a planar or non-planar geometry.

According further to the system described herein, a method for performing chemical detection and analysis includes ionizing a sample in an ion mobility spectrometer (IMS) device having a drift tube that includes a first end with a sample inlet and a second end that is downstream from the first end. Ions from ionization of the sample are introduced into the drift tube. The method further includes controlling at least one voltage pulse to a gate grid coupled to the second end of the drift tube to selectively gate ions for analysis. An analysis on the gated ions is performed using a high field asymmetric waveform ion mobility spectrometer (FAIMS) device coupled downstream from the gate grid. The FAIMS device may be coupled orthogonally to a flow direction of the ions through the drift tube of the IMS device. The control of the at least one voltage pulse to the gate grid may correspond to drift time of an ion of interest. The FAIMS device may be driven using an asymmetrical waveform, such as a rectangular waveform, although other asymmetrical waveforms may also be used. The method may further include controlling operations in connection with at least two operational modes corresponding to operations of the IMS device and the FAIMS device. Characteristics of the ionization of the sample may be determined according to a particular operational mode of the at least two operational modes. The FAIMS device may have a planar or non-planar geometry. The method may further include using at least one gas flow to enhance separation of ions in the FAIMS device, and in which the at least one gas flow includes at least one of: air, a gas other than air, or a mixture of air and other gases or substances.

According further to the system described herein, a non-transitory computer readable medium stores software for controlling chemical detection and analysis processes. The software includes executable code that controls ionizing of a sample at a frequency determined according to an operational mode of a chemical detection and analysis system. Executable code is provided that determines a drift time of an ion of interest through a drift tube of an ion mobility spectrometer (IMS) device. Executable code is provided that controls at least one voltage pulse of a gate grid coupled to the drift tube of the IMS device, in which controlling selectively gates ions for analysis by a high field asymmetric waveform ion mobility spectrometer (FAIMS) device coupled downstream from the gate grid. Control of the at least one voltage pulse to the gate grid corresponds to drift time of an ion of interest. The FAIMS device may be driven using an asymmetrical waveform, such as a rectangular waveform, although other asymmetrical waveforms may also be used. Executable code may be provided that controls operations in connection with at least two operational modes corresponding to operations of the IMS device and the FAIMS device.

BRIEF DESCRIPTION OF THE DRAWINGS

Embodiments of the system described herein are explained with reference to the several figures of the drawings, which are briefly described as follows.

DETAILED DESCRIPTION OF VARIOUS EMBODIMENTS

The system described herein provides for use of combined orthogonal techniques, such as low (IMS) and high (FAIMS) field mobility techniques, to offer several advantages including low cost, no vacuum required, and the generation of 2-D spectra for enhanced detection and identification. The two analytical devices may be operated in different modes, which results in overall flexibility by adapting the hyphenated instrument to the application's requirements. With the IMS-FAIMS hardware level flexibility, the instruments may be configured and optimized to exploit different trade-offs suitable for a variety of detection scenarios of for different lists of target compounds.

Figure 1A:
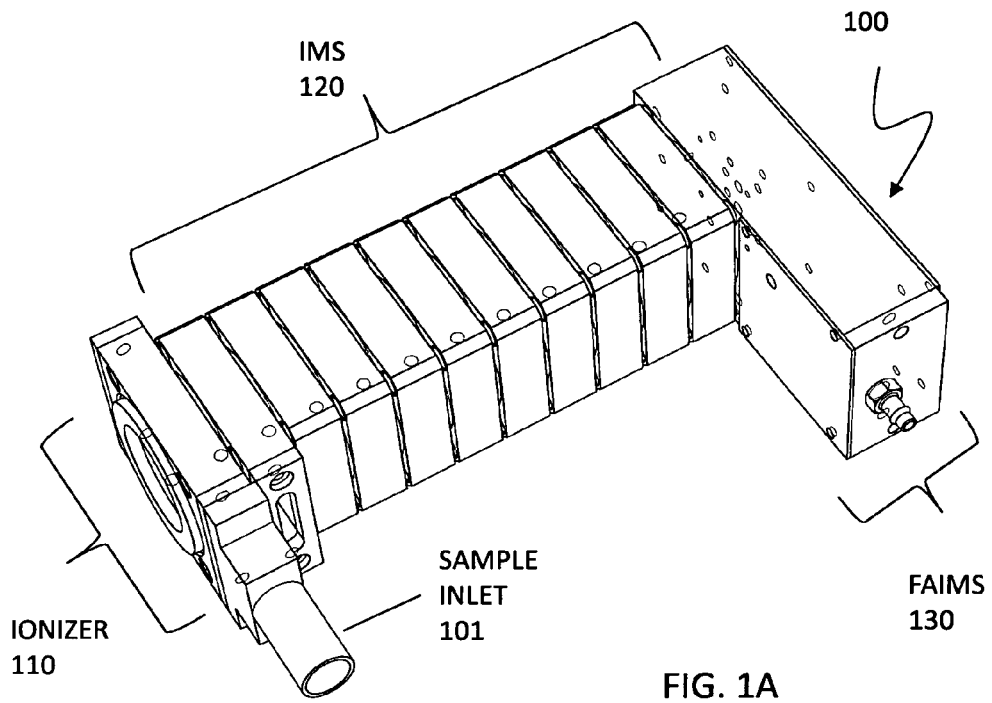
FIGS. 1A and 1B are schematic illustrations of a system that includes interfacing IMS and FAIMS devices according to an embodiment of the system described herein.
Figure 1B:
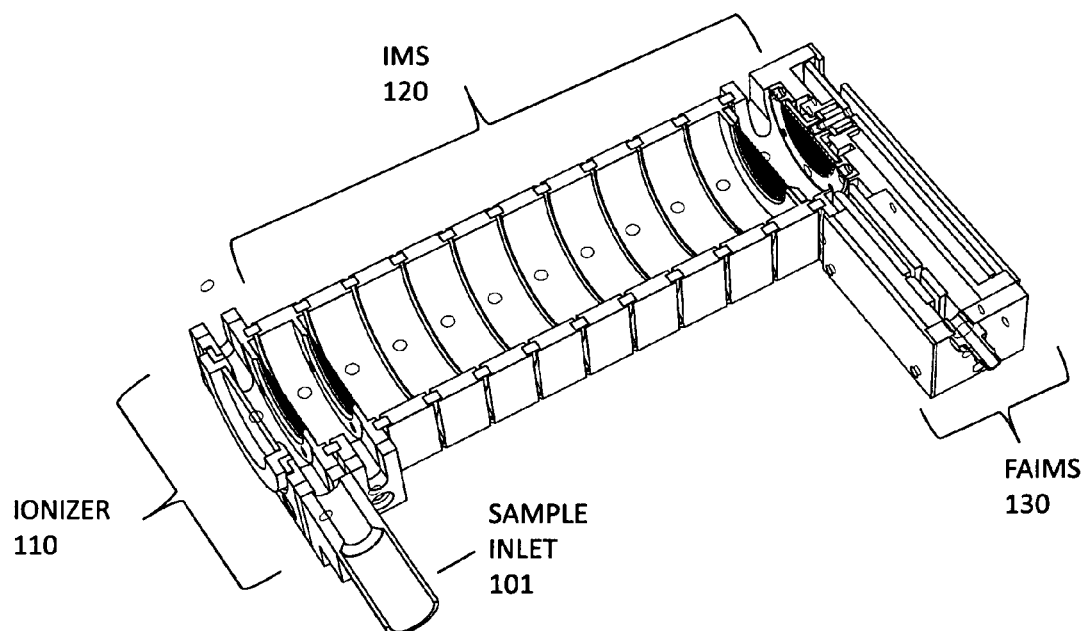

FIGS. 1A and 1B are schematic illustrations of a system 100 that includes interfacing IMS and FAIMS devices. FIG. 1A is a schematic view of the system 100 and FIG. 1B shows a cross-sectional view. The system 100 may be used to generate two dimensional data sets including drift time chromatograms and compensation voltage spectra. The system 100 may include an ionizer/ion source 110, a IMS device 120 including a drift tube, and an FAIMS device 130 (single and/or array of devices) placed at a 90 degree angle at the IMS drift tube device 120. The ionizer/ion source 110 may provide a continuous or a pulsed ion current depending on an operational mode. In an embodiment, the ionizer/ion source 110 may include a pulsed ion source, such as a spark ion source, that may send either individual packets of ions or a continuous flow of ions by varying the frequency. Additionally or alternatively, a continuous ion source may be used including a DC corona or a radioactive source via an ion gate placed at the entrance of the IMS drift tube 120. In an embodiment, the IMS drift tube device 120 may be manufactured by Implant Sciences of Wilmington, Mass. The IMS device 120 and the FAIMS device 130 may be independent and their respective electrometer circuits may be mounted on the same printed circuit board for optimum integration. In this configuration the IMS 120 may be used as a front-end filter for the FAIMS 130. Such a configuration may accomplish at least two goals: (1) pre-separation of target analytes and (2) only ions are injected into the FAIMS gas flow and driven by the gas flow into the analytical gap of the FAIMS device 130, hence keeping it free of moisture and other contaminants.

Figure 2A:
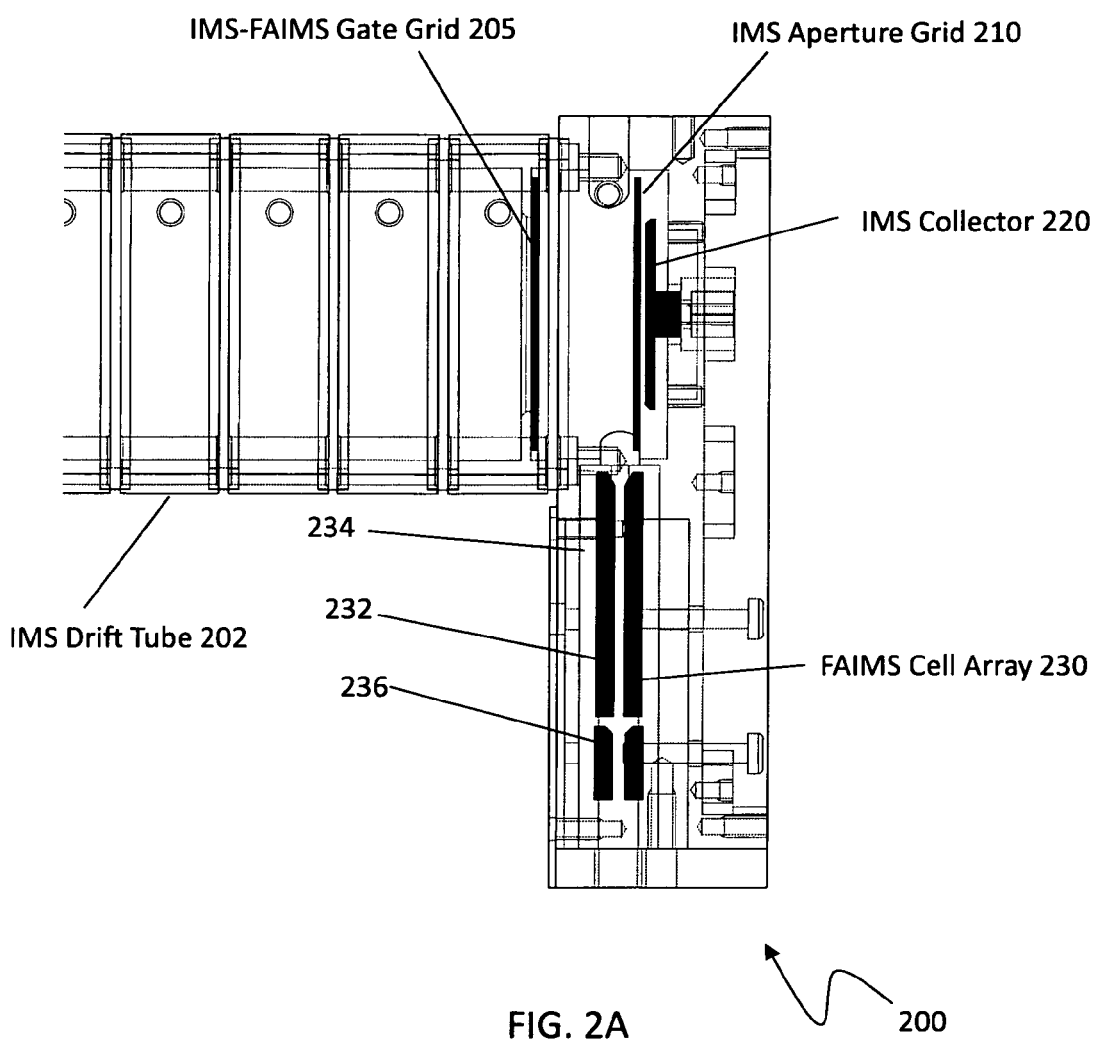
FIG. 2A is a schematic illustration showing a biased gate grid positioned at the end of an IMS drift tube according to an embodiment of the system described herein.

FIG. 2A is a schematic illustration 200 showing a biased gate grid 205 positioned at the end of an IMS drift tube 202 according to an embodiment of the system described herein. A pulsed voltage is applied to the gate grid 205 to switch from IMS to FAIMS modes and vice versa. A FAIMS device 230 may be inserted off-axis, e.g. at 90 degrees, between the gate grid 205 and an IMS aperture grid 210 and IMS collector 220. When the voltage on the gate grid 205 is switched to zero, a field free region is established and the suspended ions are pneumatically entrained at a 90 degree angle into the cells of the FAIMS device 230 using a gas flow (see FIG. 2B). The ion evacuation time determines the number of grid pulses per sampling cycle. The IMS aperture grid 210 may establish a field in the trap volume and guide ions towards the IMS collector 220.

In an embodiment, the FAIMS device 230 may include five parallel stainless steel plates 232 (e.g., 5 mm wide, 15 mm long, and 1 mm thick) making four FAIMS cells intended to operate in parallel. The plates 232 may be encased and recessed in one or more supports 234 (e.g., a Polyetheretherketone (PEEK) support measuring 8 mm wide, 18 mm long, 3 mm thick) that provides mechanical stability and electrical insulation. In parallel with the FAIMS plates is another set of five shorter (e.g., 2 mm long) detector plates 236 all connected together to generate a single signal. The plates may be fastened to the supports by high temperature epoxy. Electrical connections to the individual plates are made via wires spot welded through holes in the support. The 0.5 mm spacing between the electrodes may be maintained by an insulated polymer spacer. The top and bottom plates are then secured to each other through the support and insulating polymer with screws to ensure mechanical stability and alignment.

The FAIMS device 230 is principally described herein in connection with a planar geometry design, which may offer several advantages including ease of manufacturing and superior resolution. However, in other embodiments of the system described herein, other non-planar geometry designs of FAIMS devices may also be used, including cylindrical, spherical, and/or other appropriate geometries (see, e.g., R. Guevremont, "High-Field Asymmetric Waveform Ion Mobility Spectrometry (FAIMS)," Canadian Journal of Analytical Sciences and Spectroscopy, Vol. 49, No. 3, 2004, pp. 105-113, which is incorporated herein by reference, for a discussion of cylindrical geometry FAIMS among other FAIMS concepts).

Figure 2B:
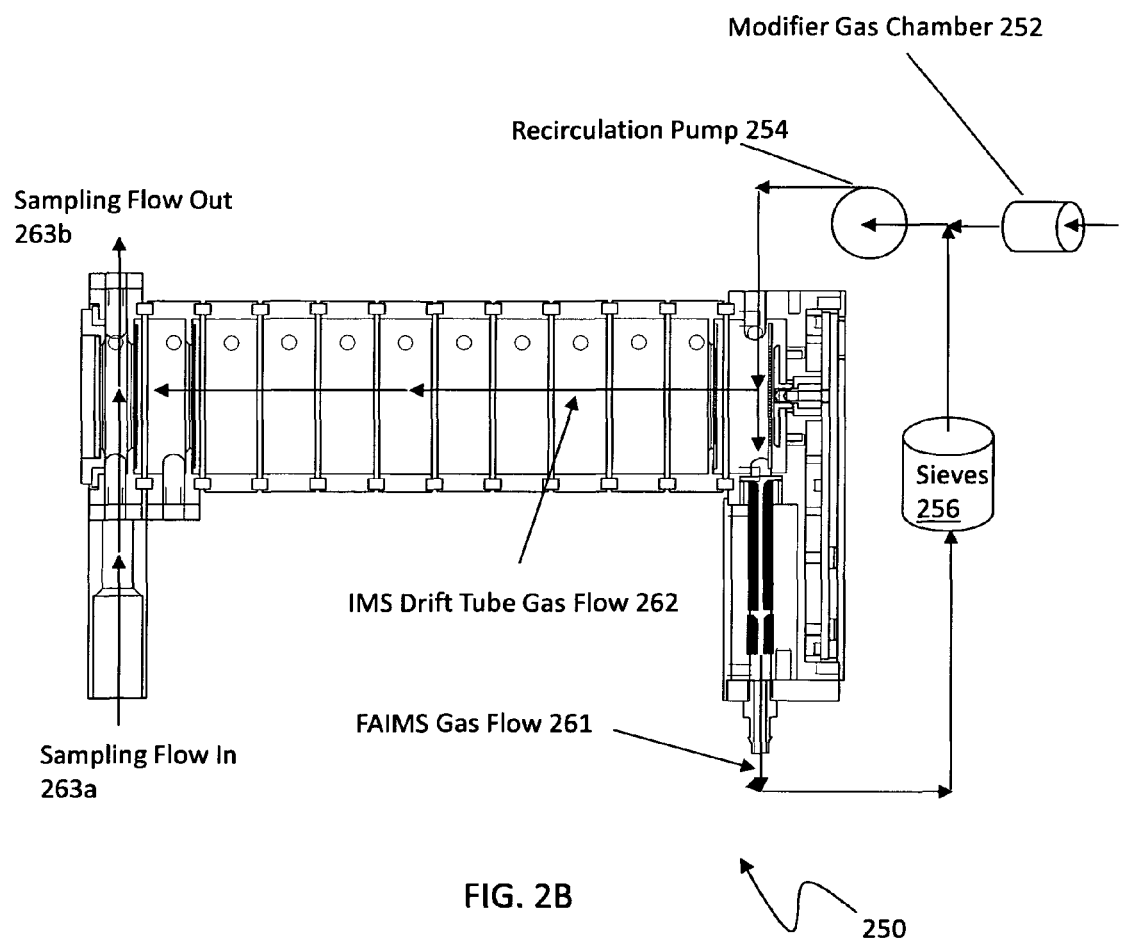
FIG. 2B is a schematic illustration showing directions of FAIMS and IMS drift tube gas flows according to an embodiment of the system described herein.

FIG. 2B is a schematic illustration 250 showing directions of FAIMS and IMS drift tube gas flows that may be used in connection with operation of the system described herein. The gas flows may include air, other gases and/or a composition of air and other gases or substances that may be generated using a modifier gas chamber 252. The illustration 250 shows the directions of the FAIMS gas flow 261 and the IMS drift tube gas flow 262. Also shown is the sampling gas flow into and out of the system (sampling gas flow in 263a and sampling gas flow out 263b). The FAIMS gas flow 261, which can be set, for example between two and ten liters per minute, may be circulated through one or more molecular sieves 254 using a pump 256. As further discussed elsewhere herein, ions are propelled through the IMS drift tube 202 in a controlled manner and are injected into the FAIMS gas flow 261 and driven thereby into the analytical gap of the FAIMS device 230. It is noted that, in the embodiment shown, the IMS drift tube gas flow 262 may be in the opposite direction of the flow of ions propelled through the IMS drift tube and injected into the FAIMS gas flow 262.

Figure 3A:
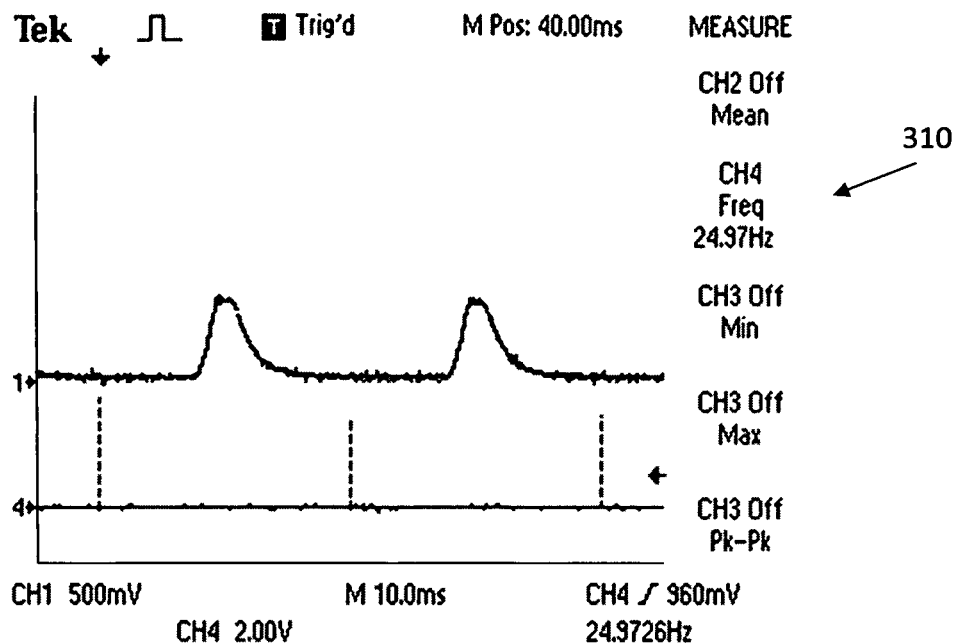
FIGS. 3A and 3B are schematic illustrations showing characteristics of two operational modes, such as an IMS mode and a FAIMS mode, of the system.
Figure 3B:
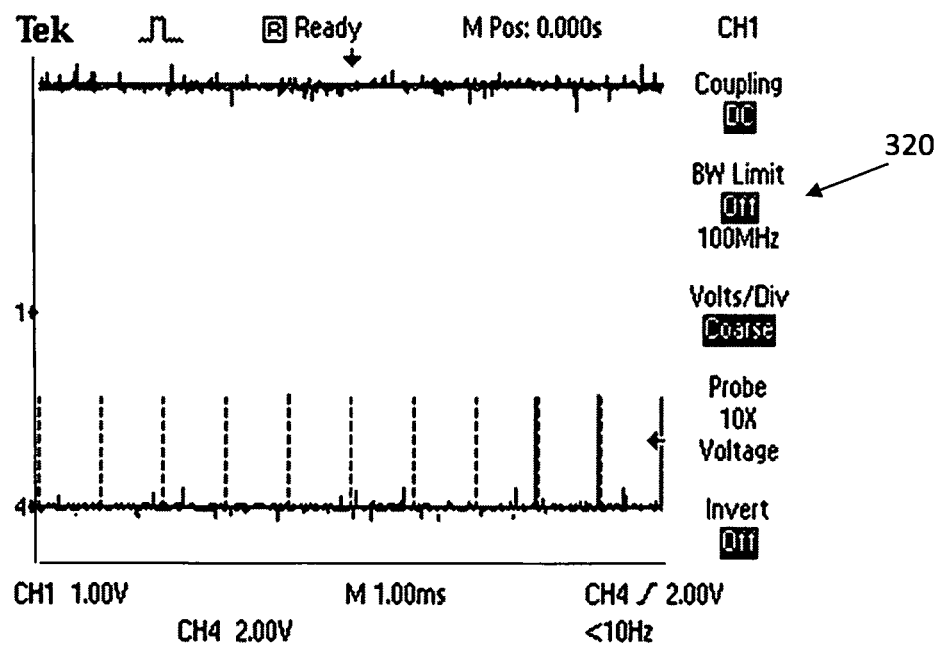

FIGS. 3A and 3B are schematic illustrations showing characteristics of two operational modes, e.g., an IMS mode and a FAIMS mode, of the system 100 that may alternate depending on the voltage bias of the gate grid and the frequency of the spark ion source according to an embodiment of the system described herein. FIG. 3A is an illustration 310 showing the characteristics for a spark ion source at 25 Hz and FIG. 3B is an illustration 320 showing the characteristics for a spark ion source at 1 kHz. The top trace in each figure shows the IMS detector response. In IMS mode, packets of ions may be injected into the IMS drift tube at a low frequency, e.g. 12 Hz, and in the FAIMS mode, the frequency can reach 1 kHz. At such a high frequency, the spark is a continuous source of ions for the FAIMS. More signal (e.g., a factor of 10) may be obtained at higher spark frequencies. Higher signals may be obtained in the FAIMS mode by increasing the field in the drift tube which becomes an ion guide.

Figure 4:
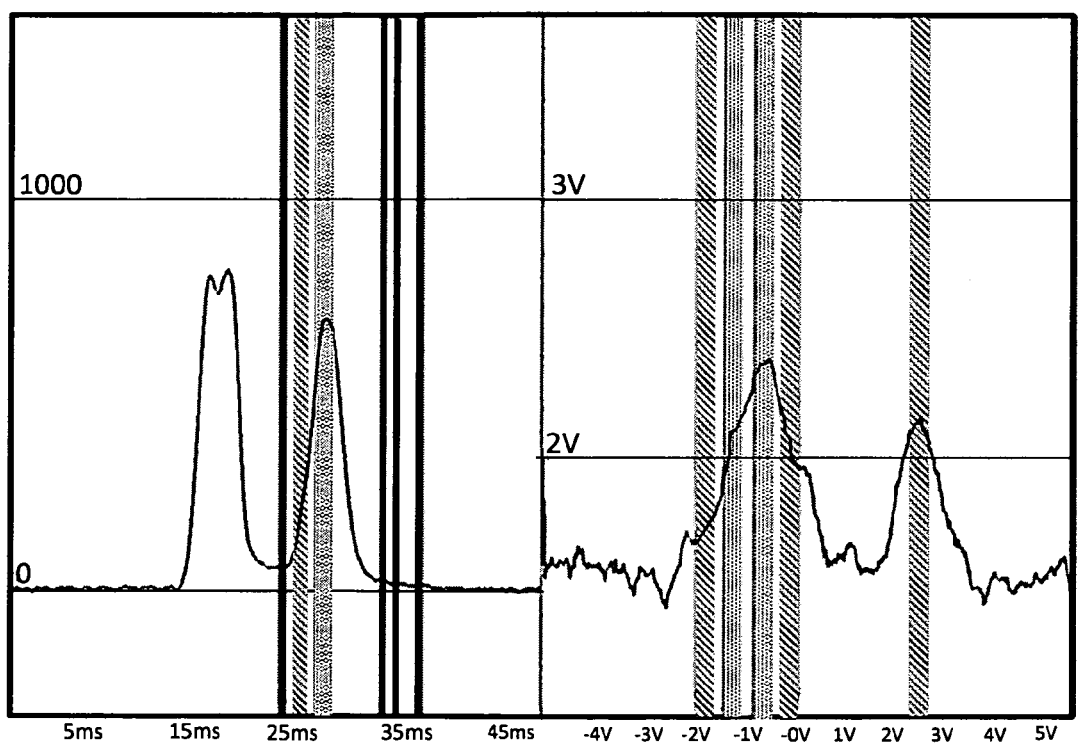
FIG. 4 is a schematic illustration showing juxtaposition of an IMS spectra and FAIMS spectra according to an embodiment of the system described herein

FIG. 4 is a schematic illustration 400 showing juxtaposition of an IMS spectra and FAIMS spectra according to an embodiment of the system described herein. The low level flexibility of this approach results in different modes of operation exploiting the trade-offs between selectivity, sensitivity, and speed. An example of an operation scenario during a sampling cycle would include generating a conventional IMS chromatogram and, upon detecting a peak, automatically switch to FAIMS mode by tuning the filter to the CV value of the detected peak. A detected FAIMS signal would serve as a confirmation as in the case of the IMS and FAIMS spectra for C4 juxtaposed in FIG. 4. Unresolved peaks in the IMS spectra corresponding to some explosives such as TNT and interferents such as hand cream but resolved in the FAIMS spectra may also be provided in accordance with the system described herein.

The IMS-FAIMS arrangement according to the system described herein provides advantageous flexibility and several other modes may also be used in connection with the system described herein. For example the gate grid 210 (FIG. 2) may serve as a gate for ions of interest. In other words, by applying a short pulse to the grid 210 at a certain time in the IMS spectrum only ions with a specific drift time will be transmitted into the field free region for FAIMS analysis. The system described herein thereby enables enhanced control for detecting ions of interest by controlling the ions that are transmitted to the FAIMS device 230 through the control of pulses corresponding to the specific drift times of the ions of interest.

The shape of a drive waveform for a FAIMS device is one of the features affecting FAIMS' resolution, transmission, and separation. Due to practical circuitry advantages, most FAIMS work to date has employed a waveform formed by summing a sinusoidal wave and its first harmonic, at twice the frequency (Equation 2), resulting in first order Fourier approximation of an asymmetric square wave.

Figure 5A:
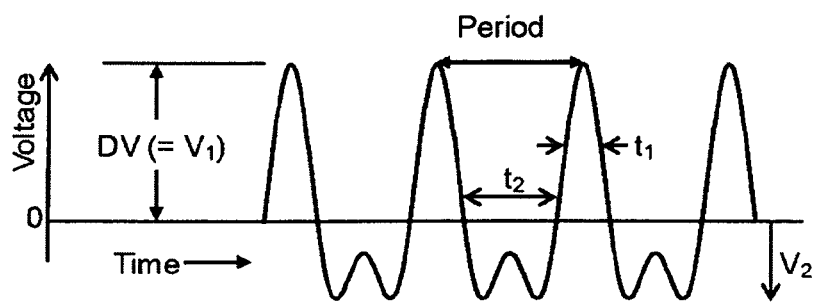
FIG. 5A is a schematic illustration showing an asymmetric sum-of-sine waveform for driving a FAIMS device.

FIG. 5A is a schematic illustration showing an asymmetric sum-of-sine waveform for, being the first order Fourier approximation of an asymmetric square wave, for driving a FAIMS device. The shape of the waveform is a parameter that contributes to the value of the experimentally measured (compound-dependent) CV for transmission of an ion. A symmetrical waveform (sine or square) should result in CV=0 V for transmission of all types of ions. Asymmetry of the waveform is required for ion separation, and is expressed by differences in the CV values.

According to the system described herein, it has been determined that a rectangular drive waveform may be advantageous for FAIMS analyses. Analytical considerations show that rectangular waveforms may improve ion separation efficiency, resolution and/or sensitivity as compared to sinusoidal waveforms. Unfortunately, the excessive power load imposed by high frequency, high voltage pulses with steep rise times has hindered the development of electronics that deliver rectangular pulses for driving separations based on differential ion mobility.

Intuitively, the use of an asymmetric square (and/or other rectangular) waveform for FAIMS would seem to maximize the differences during the high and low field portions of the electric field. These high to low periods of the waveform permit an ion to experience a maximum of unequal voltages maximizing the CV. However, in previous studies, there have been concerns that the time it takes an ion to respond to the idealized asymmetric square waveform and reach "steady state," or terminal, drift velocity might be sufficiently long to introduce error due to the transient electric field. It has been shown that, to the first order, this can be neglected if the time for reaching terminal velocity is small relative to the total drift time. Since the estimated time necessary to reach this velocity in a transient electric field is in the picosecond range and the drift time is in the millisecond range, this factor can therefore be ignored.

Figure 5B:
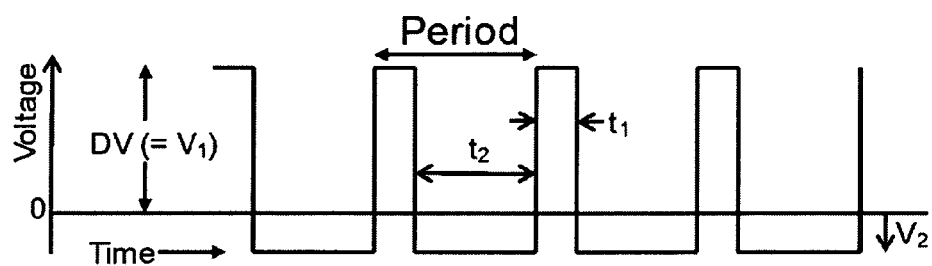
FIG. 5B shows a rectangular waveform that may be used in connection with driving a FAIMS device according to the system described herein.

FIG. 5B shows a rectangular waveform that may be used in connection with driving a FAIMS device according to the system described herein. In an embodiment, the system described herein provides for generating a square waveform to drive the FAIMS device. The method may include using direct transistor switching at high speed and at reasonable power losses. The choice of high voltage (>1000 V) fast transistors (FETs) with low output capacitance may be limited. On one hand, the 1500 V transistors are very slow and on the other, the 1200 V FETs have large output capacitances making the switching at high speed power consuming. 800 V transistors or FETs (which are fast and have low output capacitances) may also be used in series to carry very high voltages in connection with the system described herein. Other techniques may also be used in connection with generating waveforms for use with the system described herein and reference is made to, for example, E. V. Krylov, et al., "Selection and generation of waveforms for differential mobility spectrometry," Review of Scientific Instruments, 81, 024101 (2010), 11 pp., which is incorporated herein by reference.

Figure 6:
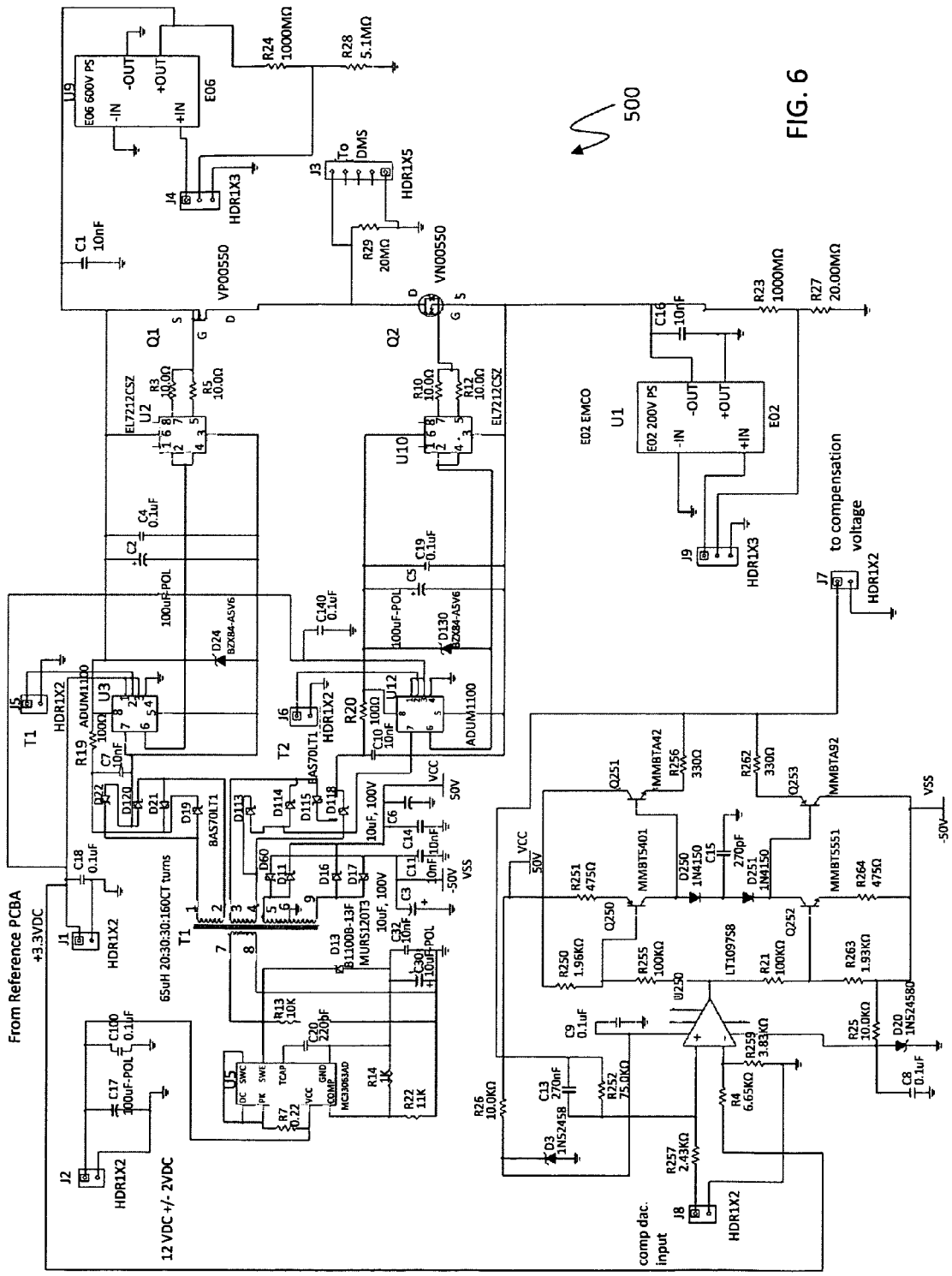
FIGS. 6 and 7 show schematic circuit diagrams for circuits that may be used according to various embodiments of the system described herein.
Figure 7:
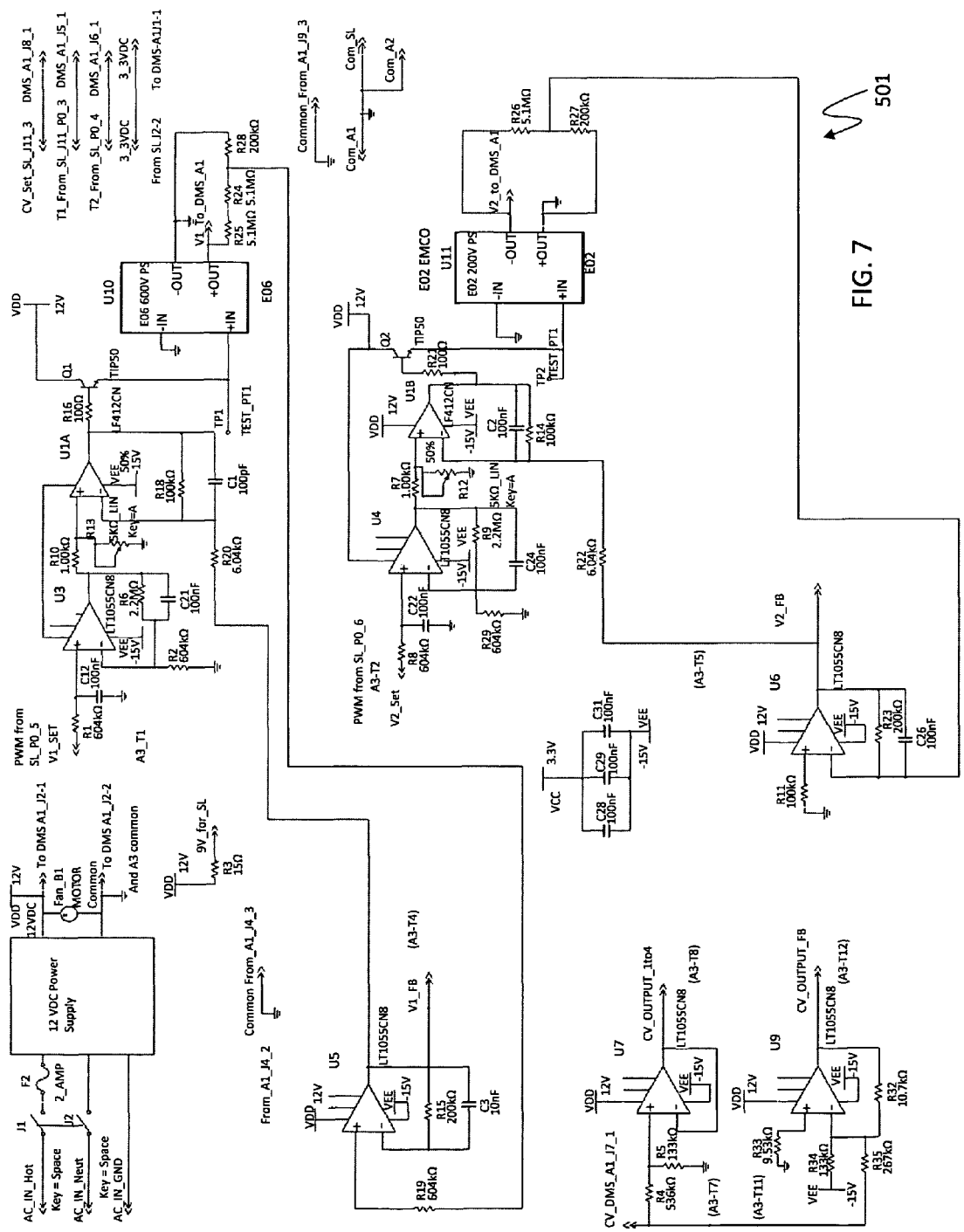

FIG. 6 shows a schematic circuit diagram 500 and FIG. 7 shows an auxiliary circuit diagram 501 for circuits that may be used according to various embodiments of the system described herein. The following modes of operation may be provided in connection with the above-noted circuits according to the system described herein:
  a. V1=+1000 V; V2=−500 V at a 2:1 duty cycle.
  b. V1=+1000 V; V2=−250 V at a 4:1 duty cycle.
  c. V1=+800 V; V2=−200 V at a 4:1 duty cycle.
Two switching waveforms may be used, one to drive the positive voltage and one for the negative voltage. These waveforms provided for adjustments to account for the circuit peculiarities and to provide the necessary dead times to assure low power switching. Three out of the four variables (V1, V2, T1, and T2) may be settable from a computer and the fourth may be deduced from the balance Equation 3.

The FAIMS driver may include a FET half-bridge (Q1, Q2), with a bus supplied by two EMCO power supplies: +400 VDC (U9) and −100 VDC (U1) connected in series and referenced to common ground (see circuit diagrams at the end of the document). Switching output is referenced to common ground via R29 (20 MOhm). The high-side FET Q1 is P-channel and bottom FET Q2 is N-channel. It has been found that a P and N combination performs better than 2 N-channel FETs. The gate drives are provided by EL7212 drivers (U2, U10). Isolated 5.6 VDC sources are generated by the U5-T1 power supply and R19, D24/R20, D130 zeners.

U3, U12 (ADUM1100) provide HV isolation and transfer from 3.3V to 5.6V signals. The logic drive signals and 3.3V bus may be provided by the outside reference board. The main source of power losses in illustrated circuits with low current, low inductance is charging and discharging of Coss of the FETs themselves. However the low Coss, high Voltage FETs may be designed for low power applications, packaged in TO-92 and cannot handle losses higher than 1 W per FET. It is also that various aspects of the circuits shown in FIGS. 6 and 7 may be simulated using computer software.

Figure 8:
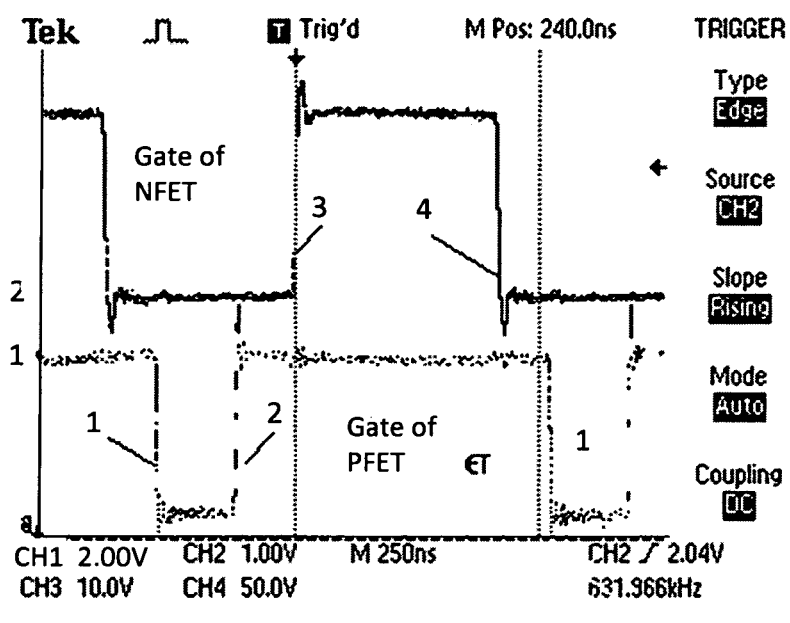
FIG. 8 is a schematic illustration showing output P and N channel gate drive waveforms according to an embodiment of the system described herein.

FIG. 8 is a schematic illustration 600 showing output P and N channel gate drive waveforms according to an embodiment of the system described herein. The 2-3 and 4-1 intervals shown on the figure are circuit dead times. The negative front 1 turns on PFET Q1 (Q2 is OFF) and brings output to +400VDC. From 1 to 2, Q1 discharges its own Coss (approx. 10 pF) and charges Q2 Coss (approx. 8 pF) by 500V. Q1 charging Q2 Coss losses may be accounted for as conduction losses. The positive front 3 turns on NFET Q2 (Q1 is OFF) and brings output to −100 VDC. From 3 to 4 Q2 discharges its own Coss and charges Q1.

While discharge losses are may be calculated as $P=V^2 \ast Coss/2$, the charge losses inside the FET due to Coss dissipation are not defined. As a first approximation, charging Coss losses may be assumed to dissipate partially in the power source resistance and partially in the opposing FETs' Rds (on).

Figure 9:
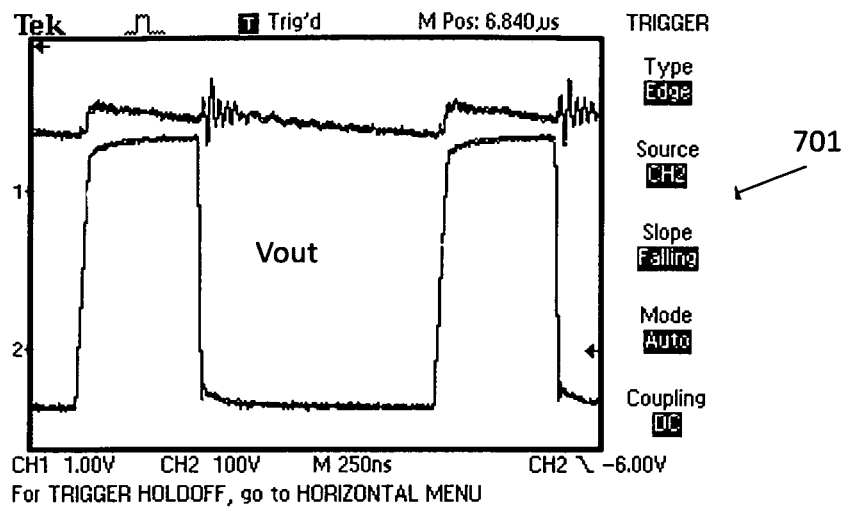
FIGS. 9-11 are schematic illustrations showing output results according to an embodiment of the system described herein.
Figure 10:
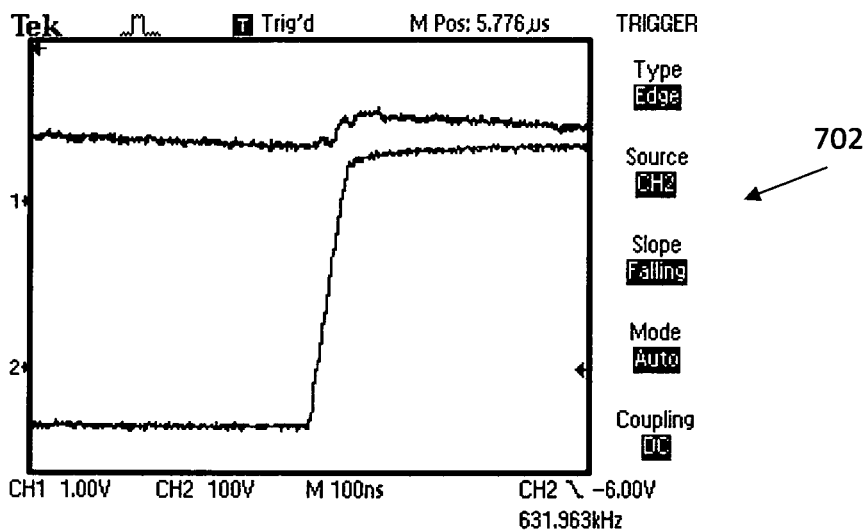
Figure 11:
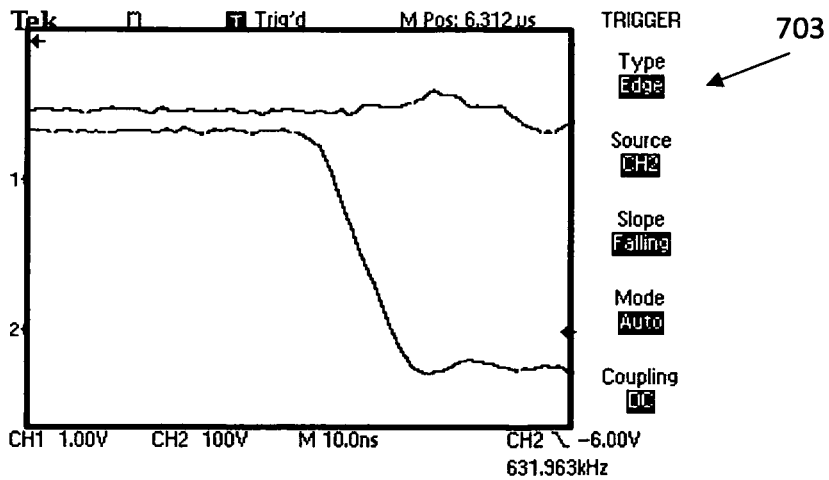

FIGS. 9-11 are schematic illustrations showing output results according to an embodiment of the system described herein. FIG. 9 is a schematic graph 701 showing a FAIMS driver output. FIG. 10 is a schematic graph 702 showing Vout-rise at higher resolution (rise time is 50 ns at dv/dt of 10V/ns). FIG. 11 is a schematic graph 703 showing Vout fall at higher resolution (fall time is 10 ns at dv/dt of −50V/ns). The horizontal slope of the output signal is due to poor instrumentation-100X probe. The gate drives of Q1, 3 selected to be 6V to maximize switching speed and reduce Coss losses. The maximum frequency of operation based on current FETs-VP0550 and VN0550 with Aavid 5752000B heat sinks should be limited to below 250 KHz to avoid destructive junction temperatures.

Two switching waveforms may be used in connection with the output, one to drive the positive voltage and one for the negative voltage. These waveforms provide for adjustments to account for the circuit peculiarities and to provide the necessary dead time to assure low power switching. Computer simulations may be used to optimize the switching scheme and hence obtain a waveform at a total power of only 0.5 watts. The computer, if desired, can continuously adjust the time portion shape of the waveform. The voltage portion of the wave shape can be adjusted but not at the high rate at which the time can be adjusted at the present time. The upper voltage and the upper time may be input as well as the lower voltage and the lower time, but is planned in operation to only vary the lower time (T2). The test set up includes the ability to set the compensation voltage to be applied to the lower electrode of the FAIMS, although an adjustable lower voltage time may also be used instead of a compensation voltage. Using this technique to keep the ions in the middle of the path so as not to strike the electrodes allows a substantial amount of circuitry to be eliminated. By adding CV to the waveform the energy is changed by $(T1-T2) \ast CV$. By changing T2 from the nominal value given by $T1 \ast V1 = T2 \ast V2$ the energy is changed by the difference in T2 times V2. Therefore the equivalence can be determined if one wants to correlate both types of data taken under similar circumstances. The use of a variable T2 represents a considerable saving in circuitry and power.

Figure 12A:
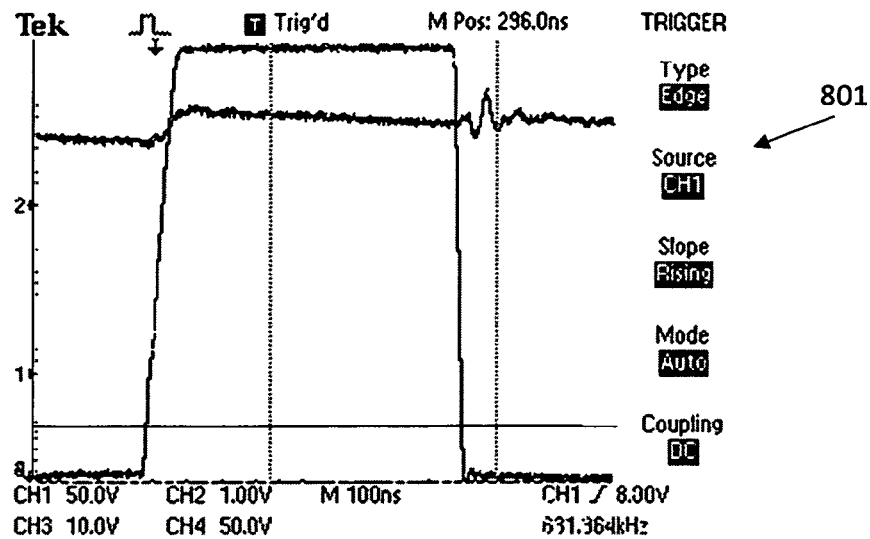
FIGS. 12A and 12B are schematic illustrations showing rectangular asymmetric waveforms usable to drive FAIMS devices along with the current required to generate such high voltages.
Figure 12B:
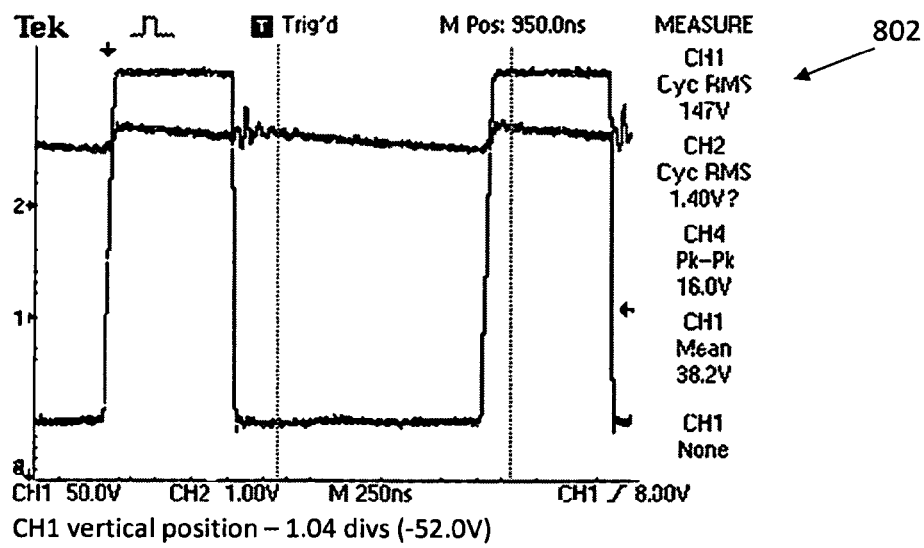

FIGS. 12A and 12B are schematic illustrations showing rectangular asymmetric waveforms usable to drive FAIMS devices along with the current required to generate such high voltages. FIG. 12A is a graph 801 showing a 500 ns up time at 400 volts. The upper curve is the current at 5 ma per div. FIG. 12B is a graph 802 showing a 30 ns rise time and faster fall time.

Figure 13:
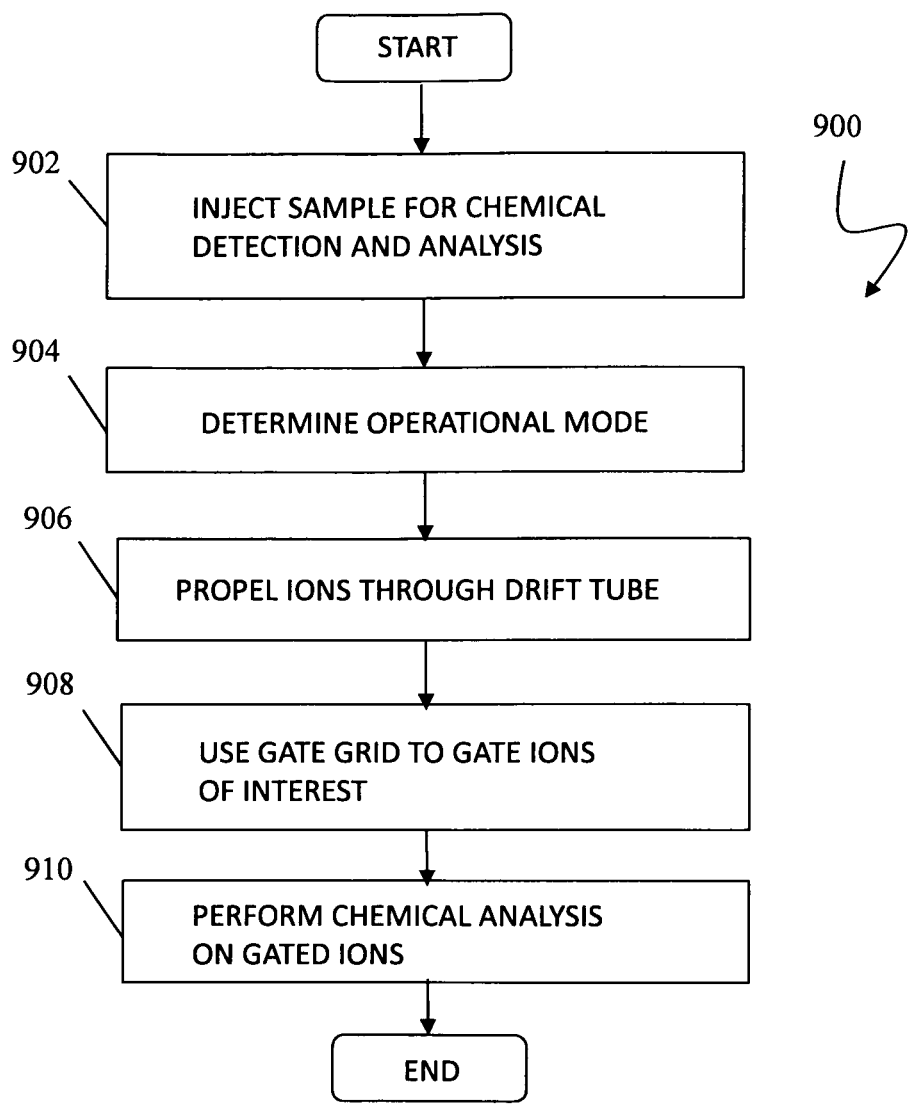
FIG. 13 is a flow diagram showing chemical analysis and detection processing steps according to an embodiment of the system described herein.

FIG. 13 is a flow diagram 900 showing chemical analysis and detection processing steps according to an embodiment of the system described herein. At a step 902, a sample gas on which chemical analysis and detection is to be performed is provided through a sample inlet to a IMS/FAIMS system according to that described herein. After the step 902, processing proceeds to a step 904 where the operational mode of the system is determined, for example, an IMS and/or FAIMS operational mode. It is also noted that operational modes may be changed during processing. After the step 904, processing proceeds to a step 906 where ion mobility spectrometry processing is performed using the IMS device to propel ions through a drift tube and in which the ions are separated according to drift time according to the determined operational mode. The frequency of the ion source may be determined by the operational mode. After the step 906, processing proceeds to a step 908 where a gate grid is controlled according to the determined operational mode. For example the gate grid may serve as a gate for ions of interest by applying a short pulse to the grid at a time in the IMS spectrum such that only the ions with a specific drift time, corresponding to application of the pulse to the grid, will be transmitted into the analytical gap of the FAIMS device. After the step 908, processing proceeds to a step 910 where chemical analysis is performed on the ions that have been separated and directed (gated) according to the system described herein. For example, in FAIMS mode, the FAIMS device may be used according to FAIMS techniques to analyze the gated ions of interest. After the step 910, processing is complete.

Various embodiments discussed herein may be combined with each other in appropriate combinations in connection with the system described herein. Additionally, in some instances, the order of steps in the flowcharts, flow diagrams and/or described flow processing may be modified, where appropriate. Further, various aspects of the system described herein may be implemented using software, hardware, a combination of software and hardware and/or other computer-implemented modules or devices having the described features and performing the described functions. Software implementations of the system described herein may include executable code that is stored in a computer readable medium and executed by one or more processors. The computer readable medium may include a computer hard drive, ROM, RAM, flash memory, portable computer storage media such as a CD-ROM, a DVD-ROM, a flash drive and/or other drive with, for example, a universal serial bus (USB) interface, and/or any other appropriate tangible or non-transitory computer readable medium or computer memory on which executable code may be stored and executed by a processor. The system described herein may be used in connection with any appropriate operating system.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A chemical detection and analysis system, comprising:
an ion mobility spectrometer (IMS) device having a drift tube that includes a first end with a sample inlet and a second end that is downstream from the first end, wherein ions from ionization of a sample input via the sample inlet are introduced into the drift tube;
a gate grid coupled to the second end of the drift tube; and
a high field asymmetric waveform ion mobility spectrometer (FAIMS) device, being of a device type different from the IMS device, coupled downstream from the IMS device and downstream from the gate grid, wherein the ions from the drift tube are selectively gated to yield gated ions via control of at least one voltage pulse to the gate grid, and wherein the gated ions are transported from the gate grid to the FAIMS device for analysis by the FAIMS device.

2. The chemical detection and analysis system according to claim 1, wherein the FAIMS device is coupled orthogonally to a flow direction of the ions through the drift tube of the IMS device.

3. The chemical detection and analysis system according to claim 1, wherein the control of the at least one voltage pulse to the gate grid corresponds to drift time of an ion of interest.

4. The chemical detection and analysis system according to claim 1, wherein the FAIMS device is driven using a rectangular waveform.

5. The chemical detection and analysis system according to claim 4, wherein the FAIMS device includes a circuit that drives the FAIMS device using the rectangular waveform.

6. The chemical detection and analysis system according to claim 1, wherein the system operates in at least two operational modes corresponding to operations of the IMS device and the FAIMS device.

7. The chemical detection and analysis system according to claim 1, wherein the FAIMS device has a planar geometry.

8. The chemical detection and analysis system according to claim 1, wherein the FAIMS device has a non-planar geometry.

9. A method for performing chemical detection and analysis, comprising:
ionizing a sample in an ion mobility spectrometer (IMS) device having a drift tube that includes a first end with a sample inlet and a second end that is downstream from the first end, wherein ions from the ionization of the sample are introduced into the drift tube;
controlling at least one voltage pulse to a gate grid coupled to the second end of the drift tube to selectively gate ions for analysis to yield gated ions at the gate grid;
performing an analysis on the gated ions using a high field asymmetric waveform ion mobility spectrometer (FAIMS) device, being of a device type different from the IMS device, coupled downstream from the IMS device and downstream from the gate grid, wherein the gated ions are transported from the gate grid to the FAIMS device for analysis by the FAIMS device.

10. The method according to claim 9, wherein the FAIMS device is coupled orthogonally to a flow direction of the ions through the drift tube of the IMS device.

11. The method according to claim 9, wherein control of the at least one voltage pulse to the gate grid corresponds to drift time of an ion of interest.

12. The method according to claim 9, wherein the FAIMS device is driven using a rectangular waveform.

13. The method according to claim 9, further comprising:
controlling operations in connection with at least two operational modes corresponding to operations of the IMS device and the FAIMS device.

14. The method according to claim 13, wherein characteristics of the ionization of the sample are determined according to a particular operational mode of the at least two operational modes.

15. The method according to claim 9, wherein the FAIMS device has a planar geometry.

16. The method according to claim 9, wherein the FAIMS device has a non-planar geometry.

17. The method according to claim 9, further comprising:
using at least one gas flow to enhance separation of ions in the FAIMS device.

18. The method according to claim 17, wherein the at least one gas flow includes at least one of: air, a gas other than air, or a mixture of air and other gases or substances.

19. A non-transitory computer readable medium storing software for controlling chemical detection and analysis processes, the software comprising:
executable code that controls ionizing of a sample at a frequency determined according to an operational mode of a chemical detection and analysis system;
executable code that determines a drift time of an ion of interest through a drift tube of an ion mobility spectrometer (IMS) device;
executable code that controls at least one voltage pulse of a gate grid coupled to the drift tube of the IMS device, wherein controlling the gate grid selectively gates ions for analysis to yield gated ions at the gate grid, wherein the gated ions are transported from the gate grid to a high field asymmetric waveform ion mobility spectrometer (FAIMS) device, being of a device type different from the IMS device, wherein the FAIMS device is coupled downstream from the IMS device and downstream from the gate grid, and wherein the gated ions are analyzed at the FAIMS device.

20. The non-transitory computer readable medium according to claim 19, wherein control of the at least one voltage pulse to the gate grid corresponds to drift time of an ion of interest.

21. The non-transitory computer readable medium according to claim 19, wherein the FAIMS device is driven using a rectangular waveform.

22. The non-transitory computer readable medium according to claim 19, wherein the software further comprises:
executable code that controls operations in connection with at least two operational modes corresponding to operations of the IMS device and the FAIMS device.

* * * * *